United States Patent [19]

Press

[11] Patent Number: 5,375,593
[45] Date of Patent: Dec. 27, 1994

[54] OXYGENATING PACIFIER

[76] Inventor: John R. Press, 222-57th St., Sea Isle City, N.J. 08243

[21] Appl. No.: 194,774

[22] Filed: Feb. 10, 1994

[51] Int. Cl.⁵ .......................... A61J 11/02; A61J 17/00
[52] U.S. Cl. ................................. 128/207.18; 606/234
[58] Field of Search ........................... 606/234–236, 606/1; 128/201.18, 201.22, 201.24, 206.21, 200.26, 207.14, 207.15, 207.18; D24/194–196

[56] References Cited

U.S. PATENT DOCUMENTS

| | | |
|---|---|---|
| D. 262,322 | 12/1981 | Mizerak . |
| 3,508,543 | 4/1970 | Aulicono . |
| 4,520,809 | 6/1985 | de Greef et al. . |
| 4,669,461 | 6/1987 | Battaglia et al. . |
| 4,708,446 | 11/1987 | Timmons et al. . |
| 4,715,379 | 12/1987 | McCormick ........................ 606/234 |
| 4,896,666 | 1/1990 | Hinkle ................. 606/235 |
| 4,969,894 | 11/1990 | Hempstead-Harris ............. 606/234 |
| 5,146,913 | 9/1992 | Khorsandian et al. ........ 128/200.26 |

Primary Examiner—Stephen C. Pellegrino
Assistant Examiner—Glenn K. Dawson
Attorney, Agent, or Firm—Caesar, Rivise, Bernstein, Cohen & Pokotilow, Ltd.

[57] ABSTRACT

A pacifier having a nipple, a mouthplate, housing assembly and a pair of nasal cannula coupled to one another and extending out of the housing so that whenever the infant has the nipple in his or her mouth the nasal cannulae are automatically directed to each nostril of the infant. A provision is made for connection of the nasal cannulae to an external oxygen source. In one embodiment the bladder is interposed between the nasal cannulae and the external oxygen source to ensure that even distribution of oxygen from the external source is provided to each nostril. Another embodiment has the nasal cannulae coupled to one another by a "T" or "Y"—connection and that "T" or "Y"—connection directly coupled to the external oxygen source.

12 Claims, 3 Drawing Sheets

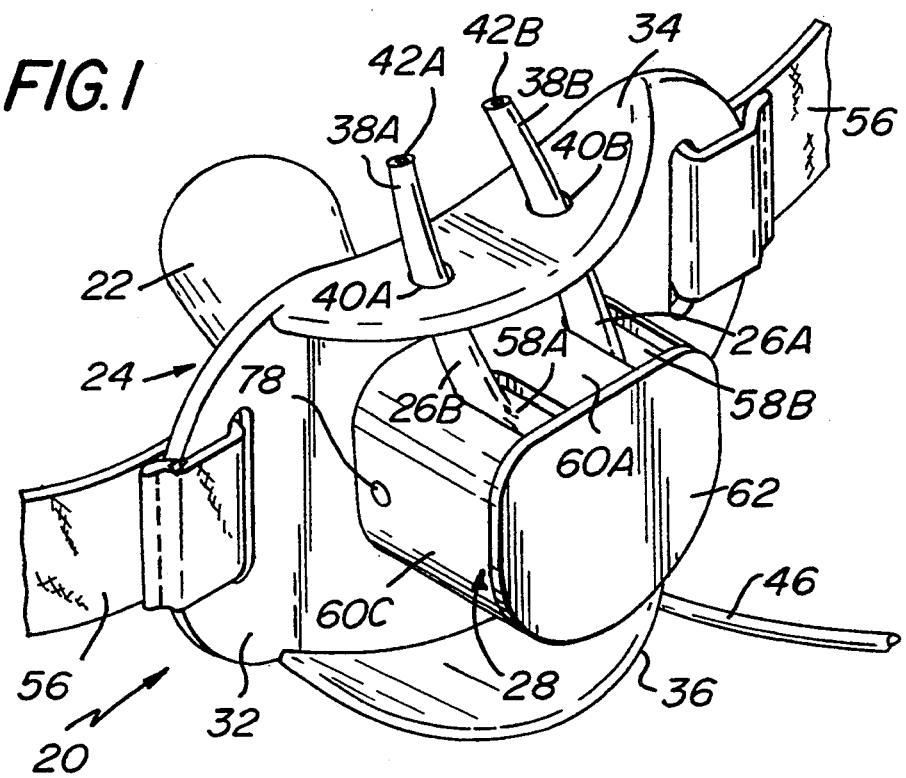
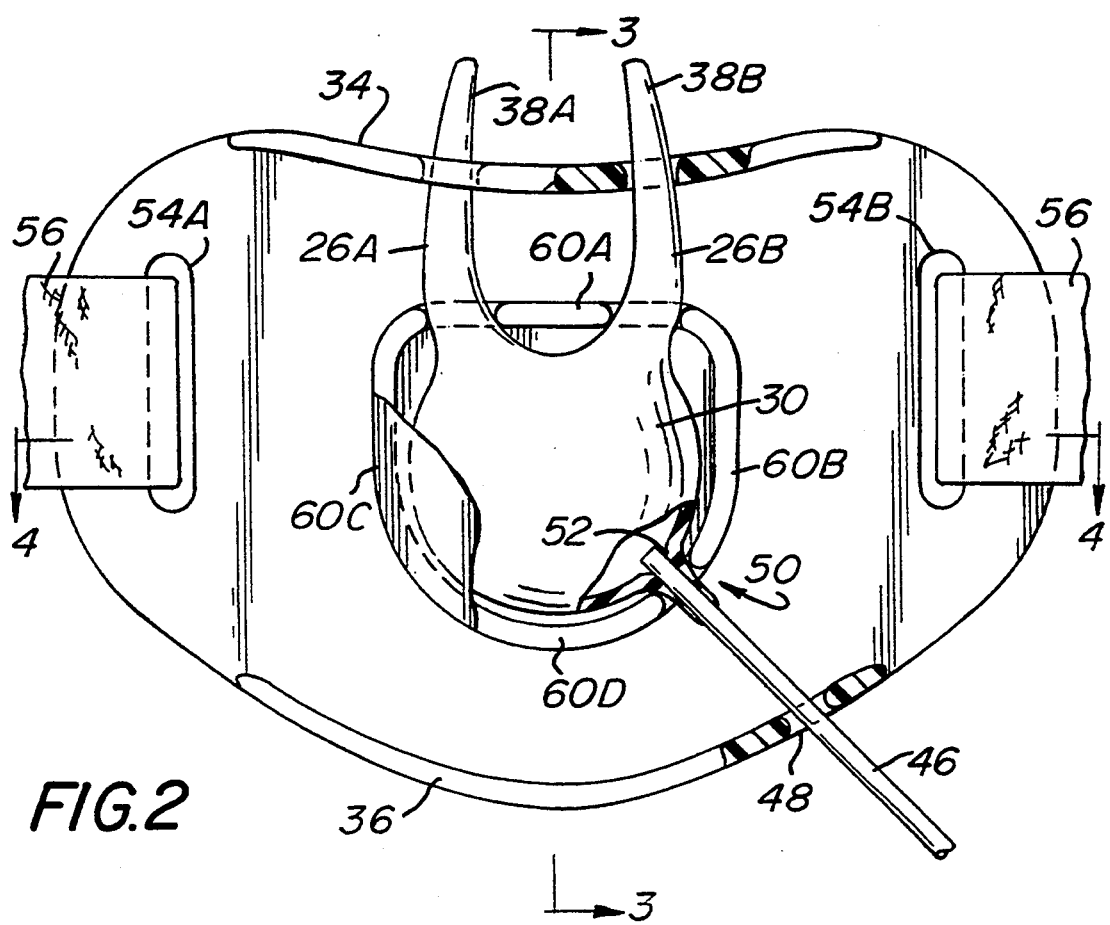

OXYGENATING PACIFIER

FIELD OF THE INVENTION

The invention pertains to devices that provide oxygen to infants. In particular, the invention pertains to oxygen devices that provide oxygen into the infant's nostrils as comfortably as possible to the infant.

BACKGROUND OF INVENTION

Providing oxygen assistance to an infant is difficult because the infant struggles whenever a face mask or nasal cannulae, the typical methods of providing oxygen assistance to a patient, are secured around the infant's face.

The following constitute examples of providing such assistance to a child without having to use a face mask found in the following U.S. Pat. Nos. 4,520,809 (de Greef et al.) and 4,669,461 (Battaglia et al.).

The apparatus disclosed by de Greef is a pacifier having a teat and shield that delivers anesthesia to an infant by providing a passageway, on the back of the pacifier shield, which is connected to an external anesthesia source. The passageway has an entrance that is connected to the external anesthesia source and also has an outlet that dispenses the anesthesia in the vicinity of the infant's nose. This passageway widens from its entrance to its outlet. However, delivery of anesthesia in specific amounts requires a more controlled method other than simply having an outlet "blow" anesthesia around the entrance of the infant's nostrils. In particular, there is no way of determining the precise amount of anesthesia being delivered at the outlet; administering anesthesia without knowing the precise amount delivered can be dangerous.

The apparatus disclosed by Battaglia is a device for providing oxygen to an infant during nursing. In particular, this device basically comprises an adjustable cuff that can be coupled to a baby bottle or directly to the mother's breast. The cuff has a port that is coupled to an external oxygen source and an outlet that permits the oxygen to be dispensed in the vicinity of the infant's nose. The cuff can pivot to vary the size of the outlet and direction of the oxygen flow. However, this device requires attachment to a bottle or to the nursing mother's breast to operate and it is not designed to provide oxygen to the infant in situations other than nursing.

In U.S. Pat. No. 3,508,543 (Aulicono), there is disclosed a device for assisting mouth-to-mouth resuscitation to an adult, as well as a child or infant, who has stopped breathing. This device comprises a mouthpiece, a mouthshield and nostril tubes. One end of the mouthpiece is inserted into the non-breathing victim while the other end is inserted into the rescuer's mouth. The nostril tubes, which are coupled to the mouthpiece, are inserted into the victim's nostrils. The mouthshield, which surrounds the midsection of the mouthpiece, forms an air tight seal against the victim's mouth to prevent air from escaping when the mouthpiece is inserted into the victim's mouth. As the rescuer blows air through the mouthpiece, the air is forced down the mouthpiece and simultaneously up into the nostril tubes, thereby providing resuscitative air into the victim's airways. While such a device may be effective for assisting in reviving a victim who has stopped breathing, it appears to be less than effective for providing continuous oxygenation to an infant who is already breathing and conscious.

Although use of nasal cannulae in conjunction with a face mask has been disclosed in U.S. Pat. No. Des. 262,322 (Mizerak) or nasal cannulae used alone in U.S. Pat. No. 4,708,446 (Timmons et. al) for oxygenating a patient, neither of these patents disclose the use of nasal cannulae used in conjunction with a pacifier for comfortably oxygenating an infant.

OBJECTS OF THE INVENTION

Accordingly, it is the general object of this invention to provide an infant oxygenation device which overcomes the disadvantages of the prior art.

It is a further object of this invention to provide for the friendly introduction to the infant of an oxygenation device.

It is still a further object of this invention to provide an infant oxygenation device which the infant does not struggle with during use.

It is yet a further object of this invention to provide an infant oxygenation device that provides equal distribution of oxygen to each nostril of the child.

SUMMARY OF THE INVENTION

These and other objects of the instant invention are achieved by providing a pacifier for an infant whereby the pacifier comprises a nipple, a mouthplate, cannulae means,. e.g., a pair of cannula, cannulae directing means, housing means and mounting means. The housing means houses a portion of the cannulae and couples the cannulae means to the cannulae directing means. The cannulae directing means automatically directs the cannulae means to the nostrils of the infant whenever the nipple is in the infant's mouth. The cannulae means also have an input port located in the housing means and the input port is arranged to be coupled to an external source of oxygen by an external oxygen line. The external source of oxygen provides oxygen to the infant through the cannulae means. The mounting means releasably secures the pacifier to the infant to hold the nipple within the infant's mouth.

In accordance with one preferred embodiment of the invention, the housing means houses a bladder coupled between the cannulae means and the input port. This bladder assures that equal distribution of oxygen from the external oxygen source is conveyed into each nostril of the infant.

DESCRIPTION OF THE DRAWINGS

Other objects and many of the attendant advantages of this invention will be readily appreciated as the same becomes better understood by reference to the following detailed description when considered in connection with the accompanying drawings wherein:

FIG. 1 is an isometric view of the preferred embodiment;

FIG. 2 is a front view of the preferred embodiment, showing the input port in a partial cut-a-way view;

DETAILED DESCRIPTION OF THE PREFERRED EMBODIMENT

Figure 3:
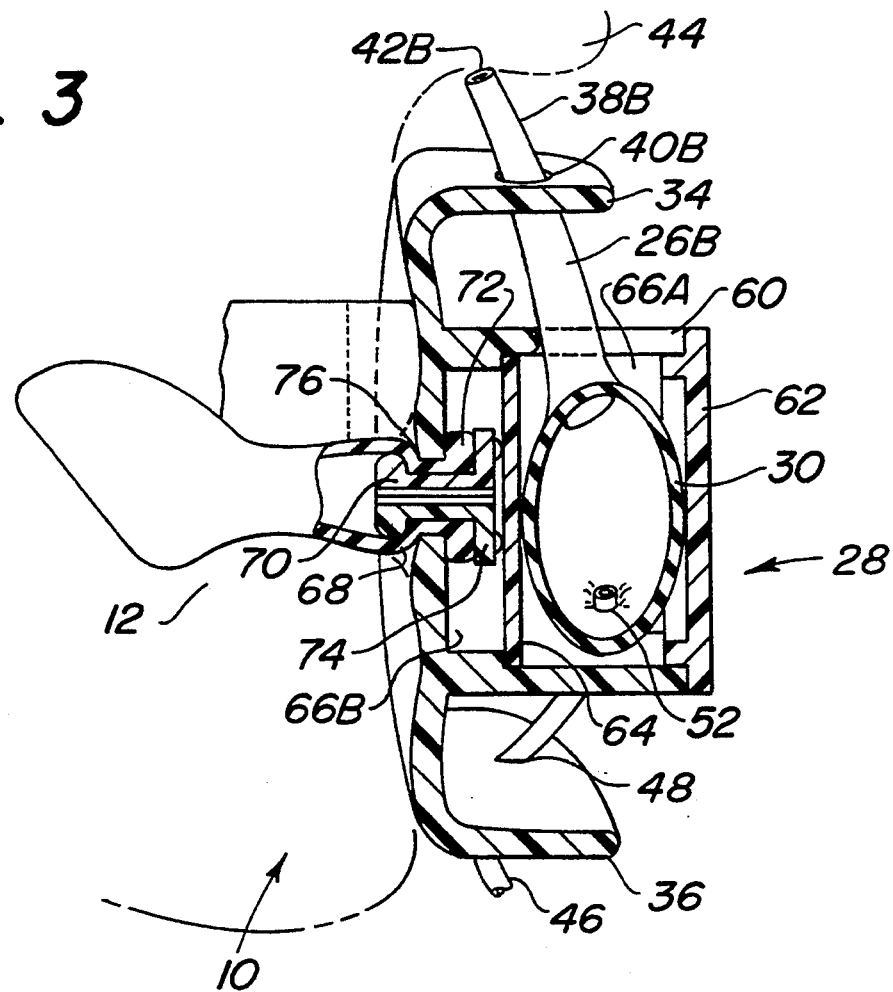
FIG. 3 is a cross-sectional view of the preferred embodiment as viewed from the side.

Referring now in detail to the various figures of the drawing wherein like reference characters refer to like parts, there is shown at 20 in FIG. 1, the preferred embodiment of an oxygenating pacifier for an infant 10 (FIG. 3). The pacifier 20 basically comprises a nipple 22, a mouthplate 24, nasal cannulae 26A and 26B, a housing assembly 28 and a bladder 30 (FIG. 2).

The nipple 22 can be any ordinary nipple used on a conventional pacifier.

The mouthplate 24 comprises a base plate 32 having an inner surface contoured to generally mate with the facial area 12 (FIG. 3) surrounding the mouth of the infant 10, an upper flange 34, a lower flange 36 and the housing assembly 28. The base plate 32 has an interior side and an exterior side. The interior side is contoured to generally mate with the facial area 12 surrounding the infant's mouth when the infant 10 is sucking on the nipple 22. The exterior side of the base plate 32 mounts the housing assembly 28.

The housing assembly 28 will be described later. Suffice it for now to state that it is a hollow member in which the bladder 30 is located and from which the cannulae 26A and 26B project. In particular, the nasal cannulae 26A and 28A project out of a pair of slots (to be described later) in the housing assembly 28 and through the upper flange 34 via holes 40A and 40B, respectively. These holes 40A and 40B offset the cannulae 26A and 26B, respectively, away from the base plate 32 of the mouthplate 24. This ensures that the nasal cannulae 26A and 26B are automatically oriented such that the cannulae tips 42A and 42B are sufficiently placed just at the entrance of the infant's nostril 44 (only one of which is shown in FIG. 3) when the nipple 22 is inside the infant's mouth. These holes 40A and 40B can be oval-shaped to permit the manual adjustment of the position of each cannulae 26A and 26B once the tips 42A and 42B are inserted at the entrance of the infant's nostrils. The cannulae ends 38A and 38B are tapered, with the tips 42A and 42B being the smallest portion of the taper, such that the ends 38A and 38B would be expelled away from the infant's mouth if the infant 10 were to ever chew or bite on those ends. Hence, the likelihood that the infant 10 would bite off and/or chew on the ends 38A and 38B is reduced by this taper.

The cannulae 26A and 26B are coupled together by way of the bladder 30, as shown in FIG. 2. In fact, the bladder 30 and cannulae 26A and 26B are formed as an integral unit of any suitable flexible material, e.g., rubber. The bladder 30 acts like a reservoir, receiving the oxygen as it flows from an external oxygen source (not shown), through an external oxygen line 46. The bladder 30 then evenly dispenses the oxygen into cannulae 26A and 26B, respectively.

The external oxygen line 46 is coupled to the mouthplate 24 by way of the lower flange 36. In particular, a hole 48 in the lower flange 36 offsets the external oxygen line 46 away from the base plate 32 of the mouthplate 24. This ensures that the external oxygen line 46 does not interfere with the infant 10 while he/she is sucking on the nipple 22.

Figure 4:
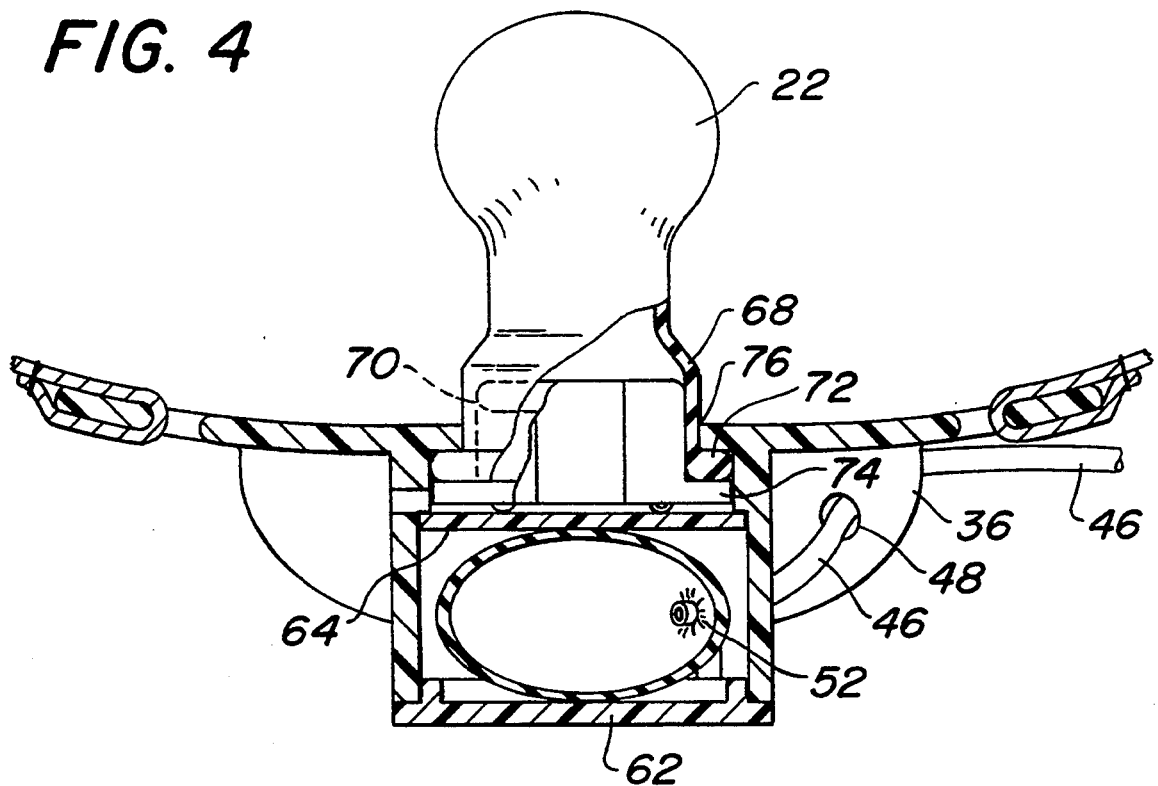
FIG. 4 is a cross-sectional view of the preferred embodiment as viewed from the top.

The external oxygen line 46 terminates inside the bladder 30 by way of an input port 50 (FIG. 2). The input port 50 is formed by the end of the external oxygen line 46 which passes through a side wall (to be described later) of the housing 28 and protrudes into the bladder 30, as most clearly seen in FIG. 4. The hole 52 in bladder 30 makes a tight seal around the end of the external oxygen line 46 to prevent any oxygen from escaping the bladder 30 at that interface.

The base plate 32 of the mouthplate 24 also has holes 54A and 54B on the right side and the left side of the mouthplate 24 which are used in conjunction with an external tether 56 that is looped and secured (e.g., tied) at its ends to the mouthplate 24. The tether 56 acts to secure the pacifier 20 to the infant's mouth 38 by affixing the tether 56 around the back of the infant's head (not shown). This mounting means is preferable where the infant 10 stops sucking (e.g., the infant 10 falls asleep) and in doing so releases any pressure which holds the nipple 22 in the infant's mouth. This mounting means thereby prevents the pacifier 20 from falling out of the infant's mouth in the absence of this pressure. Alternatively, if the infant 10 were to fall asleep (i.e., where the child is not in a state where he/she will struggle with a face mask) the pacifier 20 could be replaced with a standard mask and/or cannulae device.

The housing assembly 28 basically comprises a sidewall 60. The sidewall 60 includes a generally planar top section 60A and a pair of slightly curved side sections 60B and 60C, and a circular arc bottom section 60D. The top section 60A has two holes 58A and 58B through which the nasal cannulae 26A and 26B project, respectively. The housing assembly 28 also comprises a front panel or cover 62 that is sealed to the front edge of the sidewall 60.

The sidewall 60 and front panel 62 are preferably transparent (e.g., clear plastic) so that the condition of the bladder 30 can be easily seen. As can be more clearly seen in FIG. 3, the housing assembly 28 has an inner wall 64. The bladder 30 is encased inside a chamber 66A defined by the space bounded by the sidewall 60, the inner wall 64, and the front panel 62. A second chamber 66B is defined by the space bounded by the sidewall 60, the inner wall 64 and the exterior side of the base plate 32.

The nipple 22 is anchored within the chamber 66B. In particular the nipple 22 has a neck 68 into which is disposed a plug-like insert 70. At the end of the nipple's neck 68 is a collar 72. The collar is tightly received in an annular groove surrounding the periphery of the plug-like insert 70. A central passageway 70A extends through the insert 70 to place the interior of the nipple in fluid communication with the interior of the chamber 66B. With the insert 70 disposed inside the neck 68 of the nipple 22, the combination of the collar 72 and one end 74 of the insert 70 are pushed through an aperture 76 in the base plate 32 of the mouthplate 24, thereby trapping the end 74 and collar 72 between the inner wall 64 and the base plate 32 of the mouthplate 24. A vent hole 78 (FIG. 1) is provided in the sidewall section 60C and is in communication with the interior of the chamber 66B.

When the infant sucks on the nipple 22, any air that is trapped inside the nipple 22 can escape through the passageway 70A in neck 68 to the interior of the chamber 66B and out through the vent hole 78.

When the oxygen line 46 is connected to a source of oxygen, that oxygen will flow through the tube 46 and into the bladder 30 where it will be dispersed and exit uniformly through the two cannulae, thereby supplying the infant with equal amounts of oxygen in each nostril.

Figure 5:
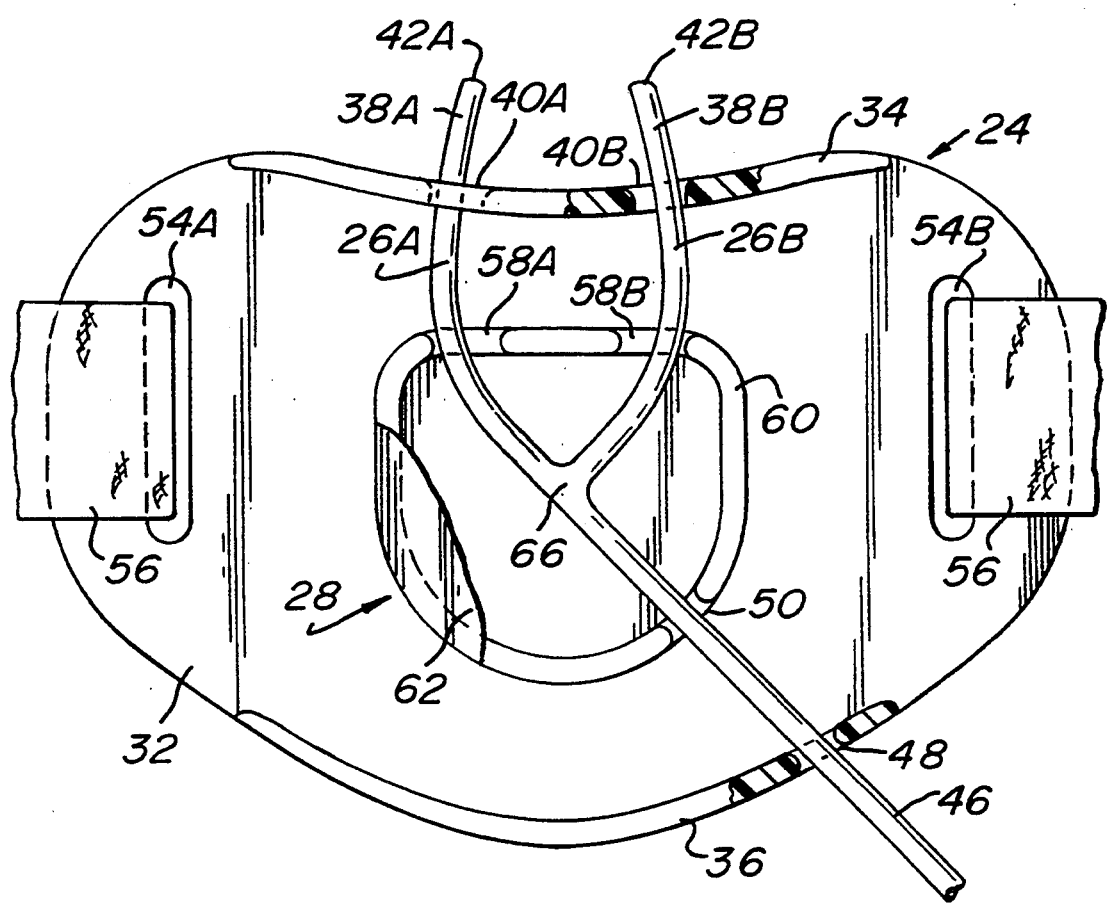
FIG. 5 is front view of a second embodiment of an oxygenating pacifier.

A second embodiment of the oxygenating pacifier is shown in FIG. 5. In this case, there is no bladder housed within the housing assembly 28. Rather, the lower ends of the nasal cannulae 26A and 26B are coupled at 90° to form a "T" connection 80 with the external oxygen line 46.

As can be appreciated with one skilled in the art, the lower ends of the nasal cannulae could easily be coupled in a "Y" connection rather than the "T" connection 80.

Without further elaboration, the foregoing will so fully illustrate my invention that others may, by applying current or future knowledge, readily adopt the same for use under various conditions of service.

I claim:

1. A pacifier for an infant comprising a nipple, a mouthplate, cannulae means, cannulae directing means, housing means, and mounting means, said mouthplate having an interior and exterior side and a left side and a right side, said nipple having an end coupled to said interior side, said housing means coupled to said exterior side of said mouthplate, said housing means housing a portion of said cannulae means therein and coupling said cannulae means to said cannulae directing means, whereupon said cannulae directing means automatically directs said cannulae means to the nostrils of the infant whenever said nipple is in the infant's mouth, said cannulae means also having an input port located in said housing means and arranged to be coupled to an external source of oxygen by an external oxygen line, said mounting means being coupled to said left and right sides of said mouthplate for releasably securing said pacifier to the infant to hold said nipple within the infant's mouth.

2. The pacifier of claim 1 wherein said cannulae means further includes a bladder coupled to said input port, said housing means housing said bladder; said bladder configured to assure that equal distribution of oxygen from said external source of oxygen is being conveyed into said nostrils of said infant.

3. The pacifier of claim 2 wherein said cannulae means comprise upper ends and wherein said upper ends of said cannulae means are tapered.

4. The pacifier of claim 2 wherein said cannulae directing means comprises an upper flange, said upper flange including at least one opening therein through which said cannulae means passes for orienting said cannulae means into the entrance of said nostrils of said infant.

5. The pacifier of claim 4 wherein said cannulae means comprise upper ends to be located in the entrance of the infant's nostrils and wherein said at least one opening is elongated to permit said cannulae means to be moved to adjust the location of said upper ends in the entrance of the infant's nostrils.

6. The pacifier of claim 2 wherein said mouthplate has a lower flange, said for lower flange orienting said external oxygen line away from said infant's face.

7. The pacifier of claim 2 wherein said mounting means comprises a tether having two ends and wherein said left side of said mouthplate has a first hole and said right side of said mouthplate has a second hole, said ends being coupled to said first and second holes, respectively, said tether being affixed to said pacifier secure said pacifier to the infant's mouth.

8. The pacifier of claim 1 wherein said cannulae means comprise upper ends and wherein said upper ends are tapered.

9. The pacifier of claim 1 wherein said cannulae directing means comprises an upper flange on said mouthplate and including at least one opening therein through which said cannulae means passes for orienting said cannulae means into the entrance of said nostrils of said infant.

10. The pacifier of claim 9 wherein said cannulae means comprise upper ends to be located in the entrance of the infant's nostrils and wherein said at least one opening is elongated to permit said cannulae means to be moved to adjust the location of said upper ends in the entrance of the infant's nostrils.

11. The pacifier of claim 1 wherein said mouthplate has a lower flange for orienting said external oxygen line away from said infant's face.

12. The pacifier of claim 1 wherein said mounting means comprises a tether having two ends and wherein said left side of said mouthplate has a first hole and said right side of said mouthplate has a second hole, said ends being coupled to said first and second holes, respectively, said tether being affixed to said pacifier to secure said pacifier to the infant's mouth.

* * * * *